United States Patent [19]
Matsuda et al.

[11] Patent Number: 5,898,000
[45] Date of Patent: Apr. 27, 1999

[54] SUBSTRATE FOR CONTROLLING GROWTH DIRECTION OF NERVE FIBERS AND PROCESS FOR PREPARING THE SAME, METHOD FOR CONTROLLING GROWTH DIRECTION OF NERVE FIBERS AND ARTIFICIAL NEURONAL NETWORK BY THE SAME

[75] Inventors: Takehisa Matsuda, Minoo; Takashi Sugawara, Ikeda; Kazuhiko Inoue, Kobe, all of Japan

[73] Assignee: Kanegafuchi Kagaku Kogyo Kabushiki Kaisha, Osaka, Japan

[21] Appl. No.: 07/712,823

[22] Filed: Jun. 10, 1991

[30] Foreign Application Priority Data

Aug. 4, 1990 [JP] Japan ................................ 2-207186

[51] Int. Cl.⁶ ..................................................... C12N 5/00
[52] U.S. Cl. ............................................ 435/395; 435/402
[58] Field of Search .................................. 435/240–243, 435/240.1, 395, 402

[56] References Cited

U.S. PATENT DOCUMENTS

| 4,554,237 | 11/1985 | Kataoka et al. . |
| 4,560,640 | 12/1985 | Ichihashi et al. . |
| 4,775,730 | 10/1988 | Gupta . |
| 4,797,348 | 1/1989 | Nakamura et al. . |
| 4,830,953 | 5/1989 | Bateman . |
| 4,996,123 | 2/1991 | Nomura et al. . |

OTHER PUBLICATIONS

*The Journal of Neuroscience*, "Controlled Outgrowth of Dissociated Neurons on Patterned Substrates", by D. Kleinfeld, K.H. Kahler, and P.E.Hockberger Nov. 1988, 8 (11), pp. 4098–4120.

*Experimental Cell Research 179*, "Cytoscribing: A Method for Micropositioning Cells and the Construction of Two–and Three–Dimensional Synthetic Tissues", by Robert J. Klebe, 1988, pp. 362–373.

*Experimental Cell Research 77*, "Behavior of Cultured Cells on Substrata of Variable Adhesiveness", by Albert Harris, 1973, pp. 285–297.

*Brain Research*, 446, "Recognition of artificial microstructures by sensory nerve fibers in culture", by Takushi Hirono, Keiichi Torimitsu, Akio Kawana and Jun Fukuda, 1988, pp. 189–194.

*Primary Examiner*—Leon B. Lankford, Jr.
*Attorney, Agent, or Firm*—Armstrong, Westerman, Hattori, McLeland & Naughton

[57] ABSTRACT

A substrate for controlling the growth direction of serve fibers charcterized in that a nerve cell adhesive substance is fixed in the form of a desired pattern and a process for preparing the substrate, a method for controlling the growth direction of nerve fibers and a neuronal network.

According to this invention, precise control of nerve fibers' growth direction is achieved.

7 Claims, 2 Drawing Sheets

Opening

SUBSTRATE FOR CONTROLLING GROWTH DIRECTION OF NERVE FIBERS AND PROCESS FOR PREPARING THE SAME, METHOD FOR CONTROLLING GROWTH DIRECTION OF NERVE FIBERS AND ARTIFICIAL NEURONAL NETWORK BY THE SAME

BACKGROUND OF THE INVENTION

The present invention relates to a substrate for controlling the growth direction of nerve fibers and a process for preparing the substrate, a method for controlling the growth direction of nerve fibers and a neuronal network.

In recent years, attempts to guide nerve fibers in a specific direction have been prompted by rapid progress in cell technology. In particular, rising interest in a neuro-computer has led to the desire for the development of a technique to guide nerve fibers in a specific direction. There is an example of the technique to control adhering portions of nerve cells as follows. A resist pattern is formed on a base plate of silicone, according to a procedure such as photolithography. After introducing alkyl groups with a silane coupling agent having an alkyl group, the resist is removed. Then, amino groups are introduced in the portions from which the resist was removed by treating with a silane coupling agent having a primary amino group. Nerve cells which are cultured on the base plate, whereon the two-dimensional fine pattern consisting of alkyl groups and amino groups is formed in the above-mentioned manner, are selectively adhered to amino groups. In this example of controlling the growth direction of nerve fibers, nerve fibers are grown along regular continuous channels which are formed according to the procedures of lithography and ion-etching on a base plate of quartz.

However, since selectivity in the adhesion of nerve cells or nerve fibers is poor according to the above-mentioned method, the desired control of the growth direction has not been achieved. Further, another problem is that the processes of preparing the substrate for culturing are complicated and expensive according to the above-mentioned method.

An object of the invention is to provide a substrate on which selectivity in the adhesion of nerve cells or nerve fibers is high and the growth direction of nerve fibers is satisfactorily controlled.

It is an object of the invention to provide a process for preparing the said substrate.

A further object of the invention is to provide a method for controlling the growth direction of nerve fibers.

It is a still further object of the invention to provide an artificial neuronal network in a form of a desired pattern.

These and other objects of the present invention will become apparent from the description hereinafter.

SUMMARY OF THE INVENTION

It has now been found that when a cell adhesive protein is fixed in a desired pattern, nerve fibers can be grown only on the portions where the cell adhesive protein is fixed.

The present invention provides
a substrate for controlling the growth direction of nerve fibers characterized in that the nerve cell adhesive substance is fixed in the form of a desired pattern,
a process for preparing a substrate for controlling the growth direction of nerve fibers which comprises
  (1) a process for fixing nerve cell non-adhesive substance in the form of a desired pattern and
  (2) a process for fixing nerve cell adhesive substance on the portions where nerve cell non-adhesive substance is not fixed,
a process for preparing a substrate for controlling the growth direction of nerve fibers which comprises
  (1) a process for fixing nerve cell non-adhesive substance on the surface of a substrate and
  (2) a process for fixing nerve cell adhesive substance in the form of a desired pattern on the substrate obtained according to the process (1),
a process for preparing a substrate for controlling the growth direction of nerve fibers which comprises
  (1) a process for fixing nerve cell adhesive substance on a surface of a substrate and
  (2) a process for fixing nerve fiber non-adhesive substance in the form of a desired pattern on the substrate obtained according to the process (1),
a method for controlling the growth direction of nerve fibers characterized in that nerve cells are cultured and in succession nerve fibers are grown on the above-mentioned substrate for controlling the growth direction of nerve fibers and
an artificial neuronal network formed by controlling the growth direction of nerve fibers.

DETAILED DESCRIPTION

Figure 1:
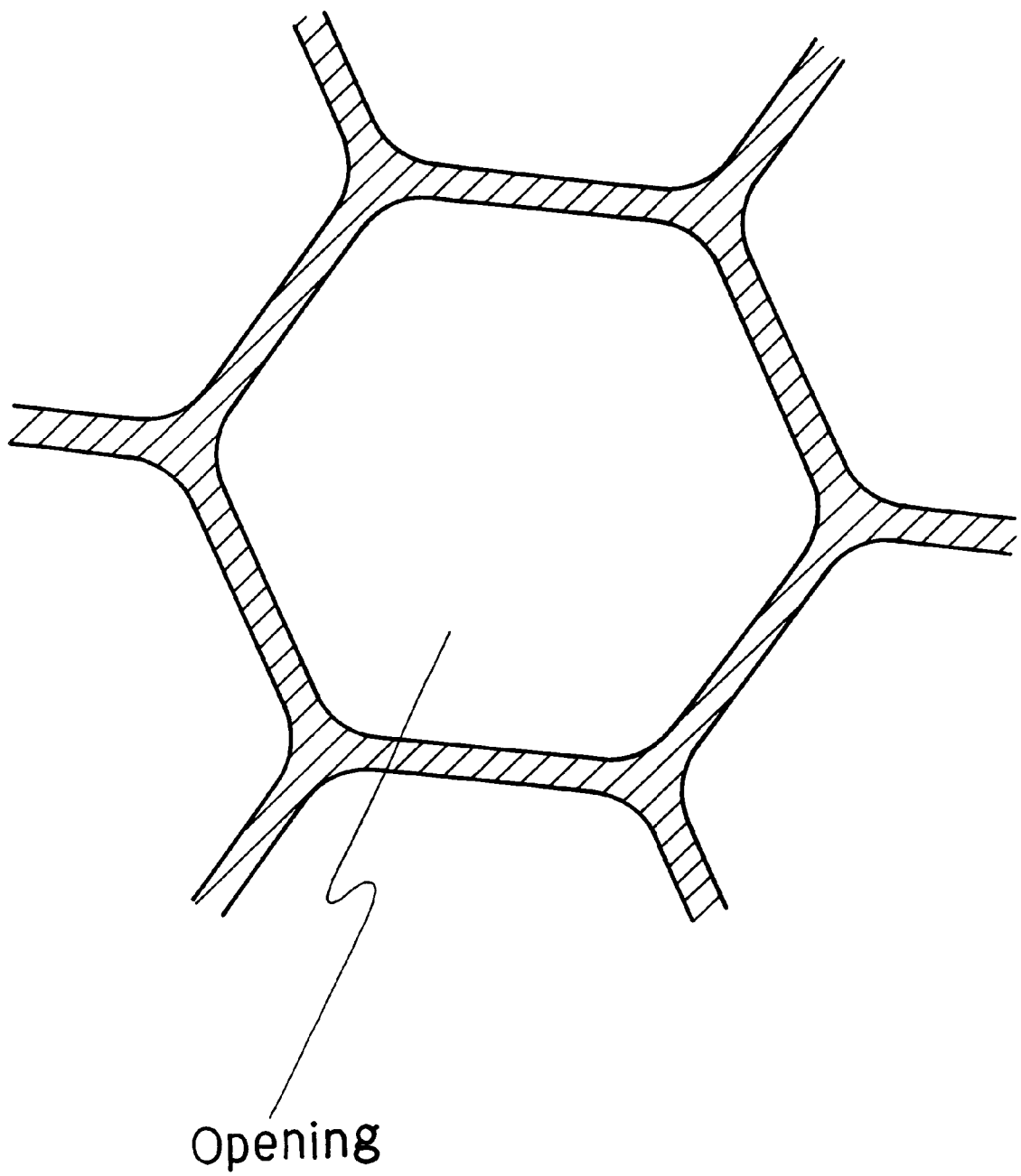
FIG. 1 is a plan view of a photomask.

The substrate for controlling the growth direction of nerve fibers of the present invention is a substrate on the surface of which a nerve cell adhesive substance is fixed in the form of a desired pattern.

All kinds of plastic, glass and metal can be used as the material to be the substrate. Plastic dishes for culture are preferable from the viewpoint that a nerve cell adhesive substance and a nerve cell non-adhesive substance can be stably fixed thereto.

Next, the process for preparing the substrate for controlling the growth direction of nerve fibers is described below.

First, a substrate is coated with a mixture of a nerve cell non-adhesive substance and a bisazide compound. A photomask having a desired pattern is set on the substrate and irradiated with ultraviolet rays. The development is carried out by washing and the above-mentioned mixture on the non-exposed portions is removed. Then, a nerve cell adhesive substance is added and adsorbed on the non-exposed portions. The cell adhesive substance which is not adsorbed is removed by washing.

As the above-mentioned nerve cell non-adhesive substance, non-ionic hydrophilic substances are preferable. For instance, a synthetic polymer such as polydimethylacrylamide can be used.

As the above-mentioned nerve cell adhesive substance, cell adhesive proteins such as collagen, laminin and fibronectin, basic peptides such as polylysine and polyarginine or basic synthetic polymers such as polyethyleneimine can be used. From the viewpoint of influence on cells, a cell adhesive protein which is a component of the tissue of the living body is preferable. Further, from the viewpoint of the fixing facility, collagen is more preferable.

A nerve cell adhesive substance can also be fixed only the portions on which nerve fiber growth is desired as follows.

Only the desired portions are irradiated through the photomask with ultraviolet rays after the substrate is coated with a mixture of a nerve cell adhesive substance and a bisazide compound. In this case, it is preferable that a nerve cell non-adhesive substance as mentioned above is fixed on the portions where the nerve cell adhesive substance is not fixed.

Next, the method of the present invention for controlling the growth direction of nerve fibers is described below.

Nerve cells are plated on the substrate of the present invention for controlling the growth direction of nerve fibers which is prepared as described above, and the cells are cultured with an adequate medium. Then, nerve cells adhere to only the portions where a nerve cell adhesive substance is fixed. Nerve fiber growth factor (NGF) is preferably added thereto one day after the adhesion, and the culturing is further continued for 3–20 days, preferably for 7–14 days. Then, nerve fibers grow up only on the portions where a nerve cell adhesive substance is fixed to give a neuronal network. As the medium used here, DMEM (Dulbecco's Modified Eagle's Medium) containing 5% of fetal horse serum and 10% of fetal bovine serum is exemplified.

The present invention is more specifically described and explained by means of the following Examples. It is to be understood that the present invention is not limited to the Example, and various changes and modifications may be made in the invention without departing from the spirit and scope thereof.

EXAMPLE 1

A mixture of 95 parts of polyN,N-dimethylacrylamide (molecular weight: about 100,000, prepared by means of radical polymerization of N,N-dimethylacrylamide, hereinafter referred to as PDMAA) and 5 parts of sodium 4,4'-diazidestilbene-2,2'-disulfonate was dissolved in methanol to give a 0.1% by weight solution.

This solution was applied on a polystyrene plate and air-dried to give a thin film with a thickness of several hundreds nm.

After a photomask with opening in it was set on the plate, an irradiation through the photomask (about 600 mJ/cm$^2$) was carried out for 30 minutes with a high pressure mercury lamp. FIG. 1 is a plan view of the photomask.

After washing enough and developing with methanol and water, the above-mentioned mixture was removed from the non-exposed portions. PDMAA was thus fixed on the polystyrene plate in the pattern of the photomask.

In succession, a solution prepared by dissolving type I collagen (purchased from Nitta Gelatin Inc.) in pH 7.4 phosphate buffer was added and the plate was allowed to stand for 1 hour at 37° C. After washing sufficiently with water, the collagen on the portions where PDMAA was fixed was removed.

Thus, a pattern of type I collagen and PDMAA was formed in the pattern of the photomask.

On the plate where a pattern of PDMAA and collagen was formed, rat adrenal medulla cells (PC12) (provided by Prof. Katsuhiko Mikoshiba of Protein Research Institute, Osaka University) were plated and cultured with DMEM (Dulbecco's Modified Eagle's Medium) containing 5% of fetal horse serum and 10% of fetal bovine serum as a medium in a CO$_2$-incubator at 37° C. After adding nerve cell growth factor (NGF) the next day, the culturing was further continued for one week to grow up.

Figure 2:
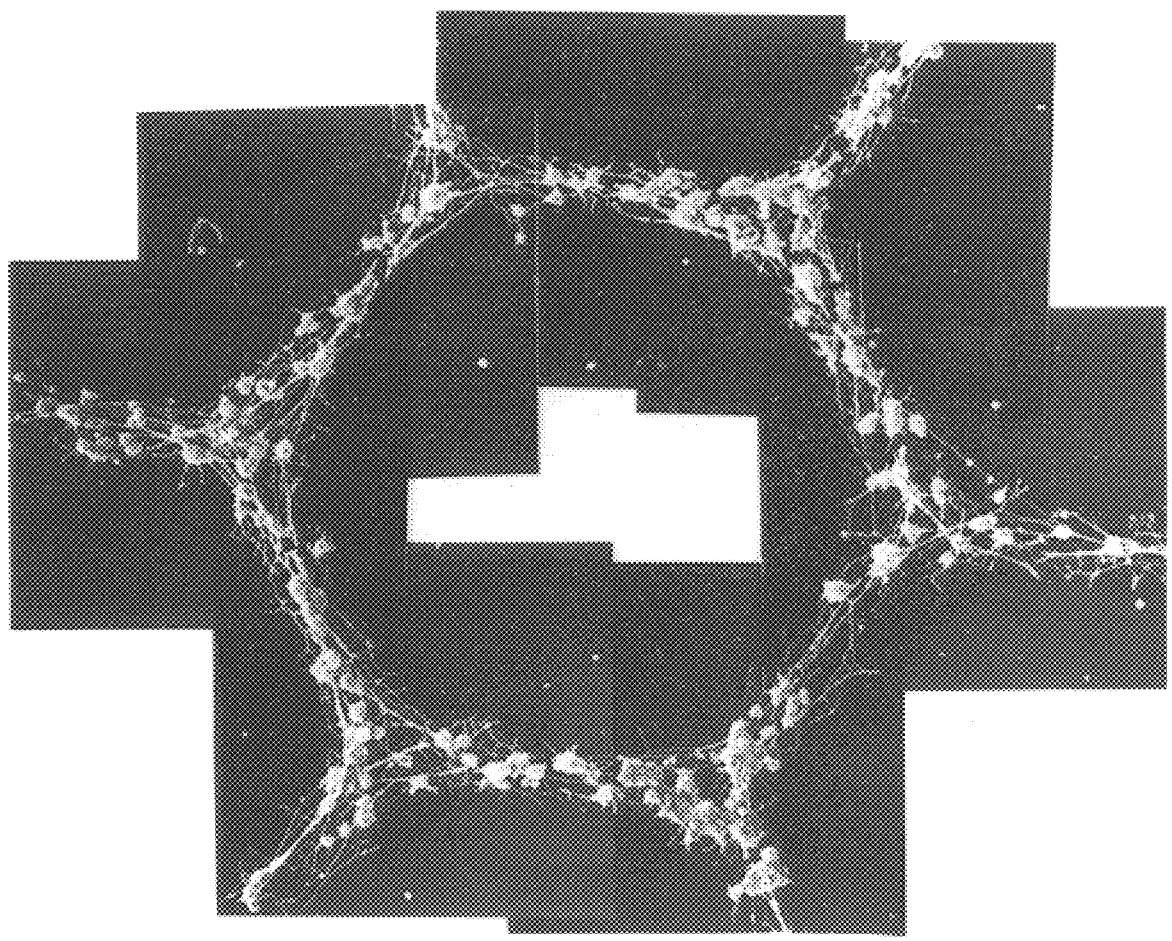
FIG. 2 is a scanning electron micrograph of nerve cells and a formed neuronal network.

One day after culturing, nerve cells (PC12) adhered only to the portions where collagen fibers were fixed. After adding NGF, nerve fibers also grew up only on the portions where collagen fibers were fixed and a neuronal network was formed. A scanning electron micrograph of the neuronal network obtained is shown in FIG. 2. As is clear from FIG. 2, the nerve fibers grown up from nerve cells were entangled with each other and a neuronal network in the pattern of the photomask was formed.

The substrate for controlling the growth direction of nerve fibers of the present invention has high selectivity in the adhesion of nerve cells and growing nerve fibers. Therefore, control of the growth direction of nerve cells can be easily achieved with high accuracy according to the present invention by culturing nerve cells and growing nerve fibers in the conventional manner. Besides, the above-mentioned substrate for controlling the growth direction of nerve fibers can be prepared according to the method of the present invention. The present invention largely contributes to the elucidation of the mechanism of neurotransmission and is connected with the development of a neuro-computer, a switching device or the like. In addition, the present invention can also be applied to medical materials which are used for reconstructin of the dissociated nerve systems.

In addition to the ingredients used in the Example, other ingredients can be used as set forth in the specification to obtain substantially the same results.

What we claim is:

1. A patterned substrate for controlling the growth direction of nerve fibers which comprises: a nerve cell non-adhesive substance comprising a non-ionic hydrophilic substance fixed in the form of a pattern on a substrate, and a nerve cell adhesive substance comprising a cell adhesive protein fixed on the portions of the substrate where the nerve fiber non-adhesive substance is not fixed, wherein at least one of the nerve cell non-adhesive substance and the nerve cell adhesive substance is fixed on the surface of the substrate by the photochemical reaction of an azide compound.

2. A process for preparing a patterned substrate for controlling the growth direction of nerve fibers which comprises: fixing a nerve cell non-adhesive substance comprising a non-ionic hydrophilic substance in the form of a pattern on the surface of a substrate, and fixing a nerve cell adhesive substance comprising a cell adhesive protein on the portions of the substrate where the nerve cell non-adhesive substance is not fixed, wherein at least one of the nerve cell non-adhesive substance and the nerve cell adhesive substance is fixed on the surface of the substrate by a photochemical reaction of an azide compound.

3. A process for preparing a patterned substrate for controlling the growth direction of nerve fibers which comprises: fixing a nerve cell adhesive substance comprising a cell adhesive protein in the form of a pattern on the surface of a substrate, and fixing a nerve cell non-adhesive substance comprising a non-ionic hydrophilic substance on the portions of the substrate where the nerve cell adhesive substance is not fixed, wherein at least one of the nerve cell non-adhesive substance and the nerve cell adhesive substance is fixed on the surface of the substrate by a photochemical reaction of an azide compound.

4. A process for preparing a patterned substrate for controlling the growth direction of nerve fibers which comprises: fixing a nerve cell non-adhesive substance comprising a non-ionic hydrophilic substance on the surface of a substrate by a photochemical reaction of an azide compound, and then fixing a nerve cell adhesive substance comprising a cell adhesive protein in the form of a pattern on the nerve cell non-adhesive substance on the surface of the substrate.

5. A process for preparing a substrate for controlling the growth direction of nerve fibers which comprises: fixing a nerve cell adhesive substance comprising a cell adhesive protein on the surface of a substrate by the photochemical reaction of an azide compound, and then fixing a nerve cell non-adhesive substance comprising a non-ionic hydrophilic substance in the form of a pattern on the nerve cell adhesive substance on the surface of the substrate.

6. The process for preparing a substrate for controlling the growth direction of nerve fibers according to any one of claims 2, 3, 4 and 5, wherein the substrate is a plastic substrate.

7. A method for controlling the growth direction of nerve fibers which comprises culturing nerve cells and nerve fibers on the patterned substrate of claim 1.

* * * * *